United States Patent [19]

Knoche

[11] 4,356,573
[45] Nov. 2, 1982

[54] BREAST PROSTHESIS

[76] Inventor: Bodo Knoche, Stoeckumer Str. 24, D-3204 Nordstemmen 4, Fed. Rep. of Germany

[21] Appl. No.: 219,858

[22] Filed: Dec. 23, 1980

[30] Foreign Application Priority Data

Aug. 19, 1980 [DE] Fed. Rep. of Germany ....... 3031223

[51] Int. Cl.³ .............................................. A61F 1/00
[52] U.S. Cl. ......................................................... 3/36
[58] Field of Search ............................................... 3/36

[56] References Cited

U.S. PATENT DOCUMENTS

| | | | |
|---|---|---|---|
| 2,108,205 | 2/1938 | Martin | 3/36 |
| 3,986,213 | 10/1976 | Lynch | 3/36 |
| 4,125,117 | 11/1978 | Lee | 3/36 X |
| 4,199,825 | 4/1980 | Knoche | 3/36 |

FOREIGN PATENT DOCUMENTS

| | | | |
|---|---|---|---|
| 5275 | 11/1979 | European Pat. Off. | 3/36 |
| 2742394 | 3/1979 | Fed. Rep. of Germany | 3/36 |
| 2802375 | 7/1979 | Fed. Rep. of Germany | 3/36 |
| 2802376 | 7/1979 | Fed. Rep. of Germany | 3/36 |
| 1132694 | 11/1968 | United Kingdom | 3/36 |

*Primary Examiner*—Clifford D. Crowder
*Attorney, Agent, or Firm*—Toren, McGeady & Stanger

[57] ABSTRACT

A breast prosthesis consists of a center part in the shape of a female breast and a border or edge part encircling the center part. The center part has a relatively thin wall in the shape of the surface of the female breast. The wall forms a cup-shaped recess containing a mixture of a silicone gel and silicone grits. The cup-shaped recess containing the mixture is closed by a thin tough cover layer forming a part of the rear surface of the prosthesis.

9 Claims, 3 Drawing Figures

BREAST PROSTHESIS

SUMMARY OF THE INVENTION

The present invention is directed to a breast prosthesis formed of a soft-elastic, porous, adherent, flesh-colored silicone rubber cross-linked with a hardener and formed in a shaped mold for insertion into a bra with the prosthesis having a center part laterally encircled by a border or edge part. The center part has a wall having a convex outer surface in the form of a female breast with the concave inner surface of the wall having a complementary shape providing the desired wall thickness of the prosthesis. The outer wall has an increased thickness in the region in which it is connected to the border part.

The present invention is an improvement on the breast prosthesis disclosed in U.S. Pat. No. 4,199,825 issued Apr. 29, 1980.

The primary object of the present invention is to prevent compression of the breast prosthesis when it is placed under pressure while maintaining, as far as is possible, the elastomechanical behavior of the prosthesis to that of a natural breast. Particularly, a weight distribution as in a natural breast is afforded to permit a natural sagging and movement of the breast prosthesis similar to that of a natural breast.

In accordance with the present invention, the center part of the prosthesis forms a recess in which a grainy paste-like mixture of silicone gel and vulcanized silicone grains or grits covered by a flexible protective layer of a very tough silicone rubber crossed-linked with a hardener and this protective layer being vulcanized to the edge encircling the cup-shaped recess.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF THE INVENTION

Figure 1:
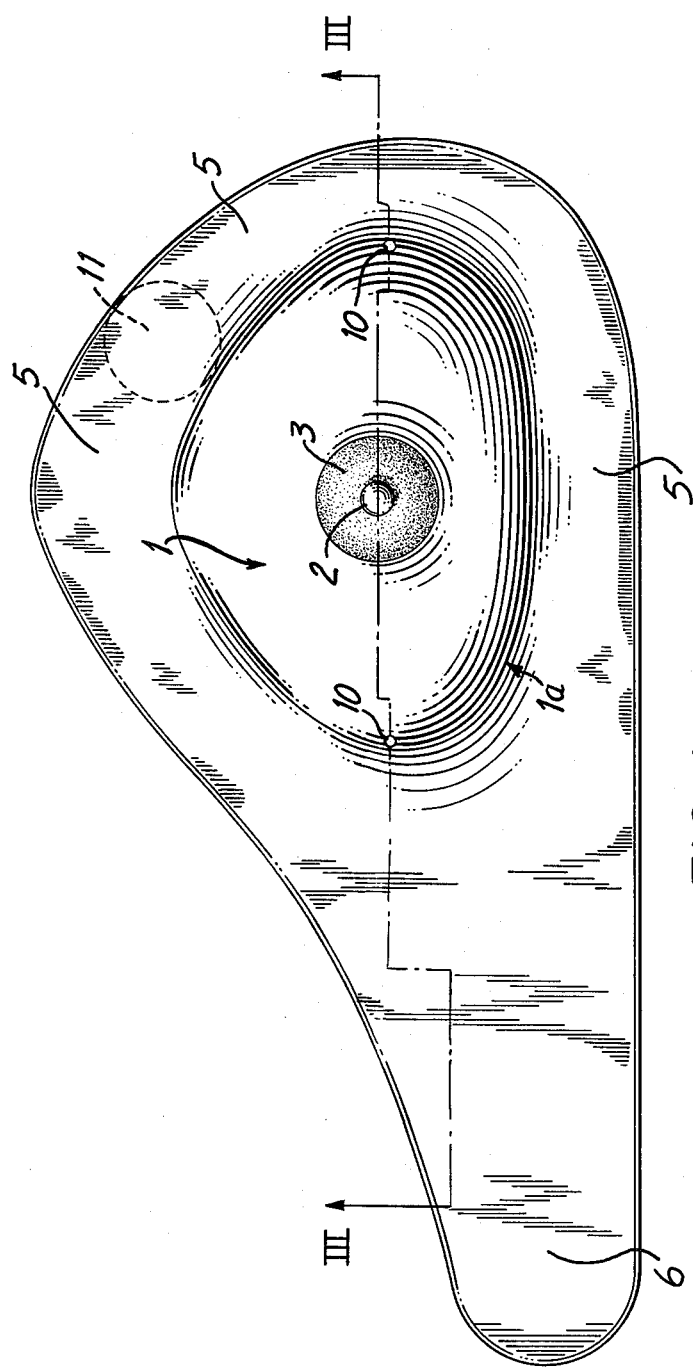
FIG. 1 is a front elevational view of the breast prosthesis incorporating the present invention.

The prosthesis shown in the drawing is produced as a casing of a soft silicone-rubber material cross-linked with a hardener. The prosthesis consists of a center part 1 having a convex outer surface 1a in the form of a female breast with a nipple 2 and an areola 3. The convex outer surface is formed by a wall having a concave inner surface made up of two zones, an inner zone 1ii and an outer zone 1i encircling the inner zone. The wall in the inner zone 1ii is thinner than the wall in the zone 1i so that a step 7 is formed encircling the inner zone. The concave surfaces of the wall in the two zones 1i and 1ii are curved similar to a female breast forming a cup-shaped recess. The wall thickness of the prosthesis in the inner zone 1ii is about 1.5 mm. Due to the elastomechanical properties of the silicone rubber material used in forming the wall, the wall has substantially the elastic properties of human skin. A border or edge part 5 encircles the outer zone 1i and forms a thin flexible edge portion the rear wall of which contacts the wearer. At the end of the border part 5 which extends toward the side of the wearer, an extension 6 is afforded which covers the armpit-lymphatic gland region.

Figure 3:
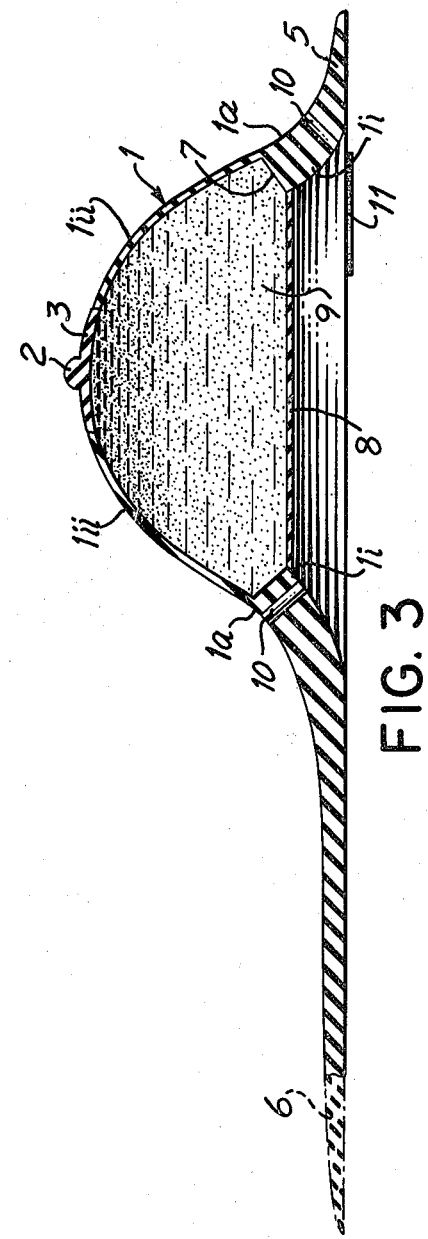
FIG. 3 is a sectional view taken along the line III—III in FIG. 1.

As can be seen in FIG. 3 the surface of the prosthesis changes from the concave surface of the outer zone 1i to a generally planar surface forming the surface which contacts the wearer. On the outer surface 1a of the center part 1 the nipple 2 and the areola 3 are formed of a very solf silicone-rubber mixture (cross-linked with a hardener). This region of the center part is made of a different mixture of silicone-rubber and hardener than the remaining portion forming the outer wall surface so that it yields a greater degree of softness.

The cup-shaped recess formed within the inner zone 1ii of the center part is covered by a protective layer 8 formed of a very tough silicone-rubber material. The layer 8 is vulcanized to the edge of the step 7, that is, it is secured to the outer zone 1i and extends completely across the cup-shaped recess. Protective layer 8 is about 1 mm thick and covers not only the inner zone 1ii but also the step 7 and makes the cup-shaped recess air and liquid tight. The cup-shaped recess between the inner zone 1ii and the protective layer 8 is filled with a grainy paste-like material consisting of a mixture of silicone-rubber gel and vulcanized silicone grains. The individual grains have the size of a grit granule and are added to the gel in an amount of about 30%. This mixture has a consistency similar to gruel.

In the increased thickness wall section of the center part encircling the cup-shaped recess, bores 10 are provided for the passage of air. These bores extend between the outer and inner surfaces of the wall forming the outer surface of the center part 1.

Figure 2:
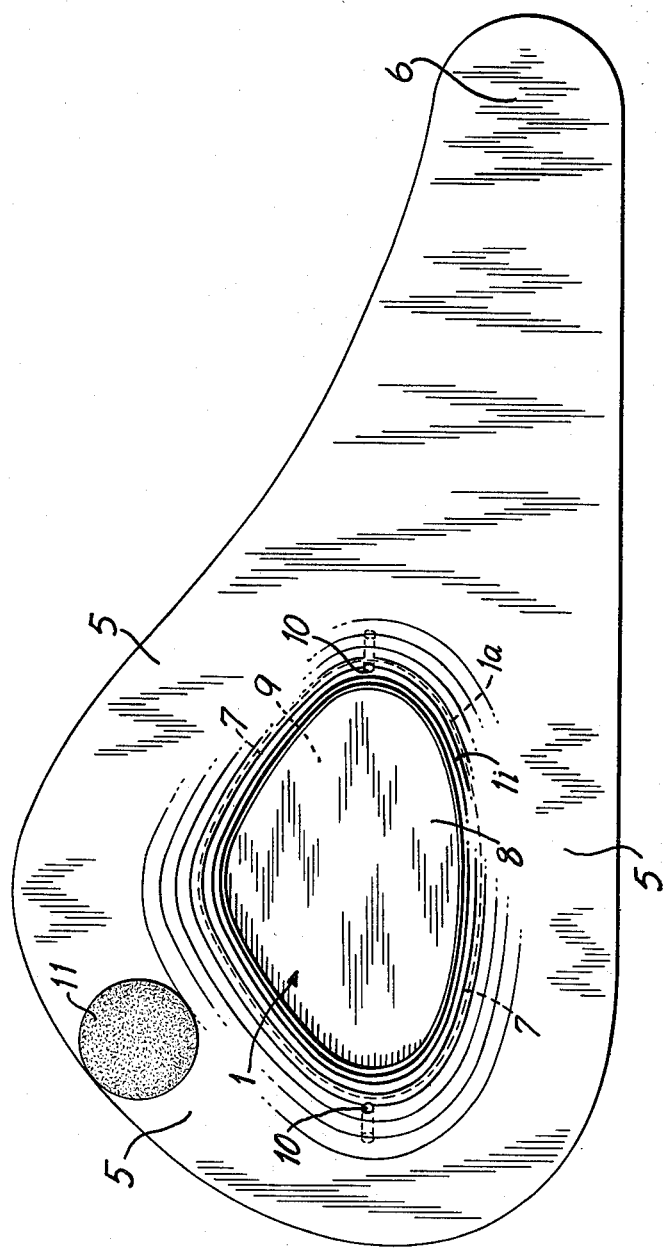
FIG. 2 is a rear elevational view of the breast prosthesis shown in FIG. 1.

On the surface of the border or edge part 5 which contacts the chest of the wearer a preferably round PVC platelet 11 of 25 mm diameter is vulcanized into a corresponding depression in the border part for attachment to a double-sided adhesive plate placed on the chest of the wearer. By means of the platelet 11 and the double-sided adhesive plate the prosthesis can be secured to the body of the wearer. As can be seen in FIG. 2 the platelet 11 is located on the border part 5 closer to the center of the wearer's chest and is positioned at a level approximately at the top of the center part of the prosthesis in the as-worn position.

The material forming the center part 1, the border part 5 with its extension 6, the material 9 filling the cup-shaped recess and its inner protective layer 8, as well as the platelet 11, is skin-colored. Further, the material forming the nipple 2 and the areola 3 is colored so that it corresponds to the color of the natural nipple and areola.

The portion of the center part 1 defining the outer zone 1i forms an increased thickness static frame for the soft movable region defined by the inner zone 1ii and this frame keeps the prosthesis in shape. The grainy paste-like filling 9 prevents the prosthesis from being compressed when pressure is applied in the region of the areola 3 or in any other direction relative to the center part. The filling 9 in combination with the protective covering layer 8 affords pressure equalization so that the center part of the prosthesis reacts resiliently to the application of any pressure. The elastic properties of the prosthesis are optimally adapted to those of a natural breast. Further, the weight of the prosthesis corresponds to that of a natural breast. This characteristic has a very positive effect on the way in which the prosthesis feels on the wearer and, as a result, on the emotional state of the prosthesis wearer because there is hardly any noticeable difference between the natural breast and the prosthesis. Particularly, it is unnecessary to adjust the shoulder straps of a bra because of any weight differences between the natural breast and the breast prosthesis and, therefore, the wearer is not made aware of her condition when wearing this prosthesis.

The breast prosthesis embodying the present invention is produced in the following manner: A casing mold consisting of a bottom part and top part for forming the outside shape of the center part and the border part is used. Initially, the areola and nipple are cast in the mold using a mixture of silicone-rubber and hardener yielding a high degree of softness and the mixture is allowed to vulcanize at about 120° C. The center part defined between the outside surface $1a$ and the inner zone $1i$ and outer zone $1ii$ of the inner surface are formed along with the border part 5 and its extension 6. A silicone rubber-hardener mixture is used in casting this portion of the prosthesis with the mixture yielding a lower degree of softness relative to the areola and nipple and it is vulcanized at about 120° C. The top part of the mold is removed and the cup-shaped recess formed within the center part up to the step formed between the inner zone $1i$ and the outer zone $1ii$ is cast with the mixture of silicone gel and silicone grit. Then the mixture of silicone rubber and hardener for forming the tough top layer 8 is spread over the surface of the mixture 9 filled in the cup-shaped recess and the edge of step 7 by means of a pencil or brush. A tight seal for the cup-shaped recess containing the mixture 9 is formed by vulcanization of the mixture of silicone rubber and hardener. Bores 10 can be formed in the prosthesis by pins inserted into the mold. After the vulcanization of the platelet 11 into its corresponding recess, the prosthesis is completed.

While specific embodiments of the invention have been shown and described in detail to illustrate the application of the inventive principles, it will be understood that the invention may be embodied otherwise without departing from such principles.

What is claimed is:

1. Breast prosthesis formed in part by mold casting a casing from a soft-elastic, porous, adherent, flesh colored silicone rubber cross-linked with a hardener, said casing comprising a center part having the shape of a female breast, and a border part extending around said center part, said center part including a generally cup-shaped wall having a convex shaped side facing outwardly and a concave shaped side facing inwardly, said convex shaped side being shaped in the form of a female breast including an areola and a nipple, said concave shaped side having a shape complementary to a female breast, said center part having an increased thickness section as compared to the remainder of said cup-shaped wall with said section forming the edge of said cup-shaped wall connected to said border part and forming an annular step extending around the inside of said cup-shaped wall and located adjacent said border part, said border part projecting laterally outwardly from said increased thickness section and forming a border surface arranged to fit against the chest of the prosthesis wearer, said step extending from said concave shaped side in the direction toward and being spaced from said border surface and having an edge spaced from said concave shaped side and being closer to said border surface, a grain-like paste mixture filling the interior of said cup-shaped wall approximately to the range of said step, said grain-like paste mixture comprising a mixture of a silicone gel and vulcanized silicone grits, and a flexible cover layer being formed of a tough silicone rubber cross-linked with a hardener extending over and in contact with the surface of said mixture and secured to said increased thickness section extending around the edge of said cup-shaped wall for retaining said mixture within said center part and said cover layer being spaced from said border surface so that said cover layer is spaced from the chest of the prosthesis wearer.

2. Breast prosthesis, as set forth in claim 1, wherein said areola and nipple being softer than the remainder of said cup-shaped wall, and said cup-shaped wall having a recess in the location of said areola and nipple with said areola and nipple being vulcanized in the recess.

3. Breast prosthesis, as set forth in claim 1, wherein said cover layer being vulcanized to said increased thickness section of said cup-shaped outer wall.

4. Breast prosthesis, as set forth in claim 1, wherein vent holes being provided in the increased thickness section at the edge of said cup-shaped wall.

5. Breast prosthesis, as set forth in claim 1, wherein said cup-shaped outer wall of said center part extending from said increased thickness section having a wall thickness of about 1.5 mm.

6. Breast prosthesis, as set forth in claim 5, wherein said cover layer having a wall thickness of about 1 mm.

7. Breast prosthesis, as set forth in claim 1, wherein said mixture of a silicone gel and vulcanized silicone grits being flesh colored.

8. Breast prosthesis, as set forth in claim 1, wherein said mixture comprises a 30% portion of silicone grit relative to said silicone gel.

9. Breast prosthesis, as set forth in claim 1, wherein a plate member being vulcanized in the surface of said border part which faces toward the chest of the wearer for securement to a double-sided adhesive platelet fixed to the chest of the wearer.

* * * * *